US00PP12028P2

(12) United States Plant Patent
Osiecki

(10) Patent No.: US PP12,028 P2
(45) Date of Patent: Jul. 31, 2001

(54) ANTHURIUM PLANT NAMED 'ATWENTY'

(75) Inventor: Marian W. Osiecki, Marianna, FL (US)

(73) Assignee: Oglesby Plants Intl. Inc., Altha, FL (US)

( * ) Notice: Subject to any disclaimer, the term of this patent is extended or adjusted under 35 U.S.C. 154(b) by 0 days.

(21) Appl. No.: 09/569,358

(22) Filed: May 11, 2000

(51) Int. Cl.[7] ..... A01H 5/00
(52) U.S. Cl. ..... Plt./367
(58) Field of Search ..... Plt./367, 369

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Anthurium plant named 'Atwenty', characterized by its dwarf growth habit; high vigor; early and freely flowering habit; large spathes in proportion to the overall plant size; spathes held slightly above or at the foliage level on straight, thick and strong peduncles; salmon pink-colored spathes with various amounts of green coloration in the lobes; bright yellow-colored spadices; and long-lasting spathes.

2 Drawing Sheets

BACKGROUND OF THE INVENTION

The present invention relates to a new and distinct cultivar of Anthurium plant, botanically known as Anthurium hybrid, and hereinafter referred to by the cultivar name Atwenty.

The new cultivar is a product of a planned and controlled breeding program conducted by the Inventor in Altha, Fla. The objective of the breeding program is to create dwarf and early-flowering potted anthurium cultivars with attractive spathe color, good spathe longevity, and short production time. The new cultivar originated from a deliberate cross by the Inventor in 1993 between the Anthurium cultivar A2, disclosed in U.S. Plant Pat. No. 10,210, as the female or seed parent and a proprietary Anthurium seedling selection identified as code number 91-94-2, as the male or pollen parent. The cultivar Atwenty was discovered and selected by the Inventor as a plant within the progeny of the stated cross in a controlled environment in Altha, Fla., in 1994.

Asexual propagation of the new cultivar by tissue culture in Altha, Fla., has shown that the unique features of this new Anthurium plant are stable and reproduced true to type in successive generations of asexual propagation.

SUMMARY OF THE INVENTION

The new Anthurium has not been observed under all possible environmental conditions. The phenotype may vary somewhat with variations in environment such as temperature, light intensity, fertilizer rate, irrigation amount and frequency, and/or propagation procedures without, however, any variance in genotype.

The following traits have been repeatedly observed and are determined to be the unique characteristics of 'Atwenty'. These characteristics in combination distinguish 'Atwenty' as a new and distinct cultivar:

1. Plants of the new Anthurium have a dwarf growth habit and are suitable for 7.5 to 15-cm containers.
2. Plants of the new Anthurium are very vigorous.
3. Plants of the new Anthurium are freely and early flowering.

4. Plants of the new Anthurium have large spathes in proportion to the overall plant size.
5. Spathes of plants of the new Anthurium are held just above the leaves on straight, thick and strong peduncles.
6. Young spathes of plants of the new Anthurium are salmon pink in color with various amounts of green coloration in the lobes.
7. Young spadices of plants of the new Anthurium are bright yellow in color.
8. Spathes of plants of the new Anthurium are long-lasting. Ornamental value is maintained for several months after maturity.
9. Attractiveness of plants of the new Anthurium is enhanced by the differently colored inflorescences at various stages of development.

Plants of the new Anthurium differ from plants of the female parent, the cultivar A2, in the following characteristics:

1. Plants of the new Anthurium are larger and more vigorous than plans of the cultivar A2.
2. Plants of the new Anthurium are more upright with a more open growth habit than plants of the cultivar A2.
3. Plants of the new Anthurium are not as freely branching as plants of the cultivar A2.
4. Plants of the new Anthurium have a slightly shorter production time, flower slightly earlier, but are not as freely flowering as plants of the cultivar A2.
5. Leaves of plants of the new Anthurium are larger, with more cordate bases and slightly longer apices than leaves of plants of the cultivar A2.
6. Young newly unfurled leaves of plants of the new Anthurium are usually darker and more brown in color than newly unfurled leaves of plants of the cultivar A2.
7. Plants of the new Anthurium have longer petioles than plants of the cultivar A2.
8. Spathes of plants of the new Anthurium are held more horizontal (less upright) and are situated slightly closer to the foliage than spathes of plants of the cultivar A2.
9. Spathes of plants of the new Anthurium are larger, more deltoid in shape, and have more cordate bases than spathes of plants of the cultivar A2.

10. Spathes of plants of the new Anthurium are slamon pink in color whereas spathes of plants of the cultivar A2 are pink in color.
11. Spathes of plants of the new Anthurium usually have some green coloration in the lobes whereas spathes of plants of the cultivar A2 do not have any green coloration.
12. Spathes of plants of the new Anthurium are glossier than spathes of plants of the cultivar A2.
13. Spathes of plants of the new Anthurium maintain color longer than spathes of plants of the cultivar A2.
14. Spathes of plants of the new Anthurium age more attractively as spathe color darkens with age whereas spathes of plants of the cultivar A2 gradually fade in color with age.
15. Young spadices of plants of the new Anthurium are bright yellow in color whereas young spadices of plants of the cultivar A2 are pink in color.

Plants of the new Anthurium differ from plants of the male parent, the proprietary seedling selection identified as code number 91-94-2, in the following characteristics:

1. Plants of the new Anthurium are smaller than plants of the selection 91-94-2.
2. Plants of the new Anthurium have smaller leaves than plants of the selection 91-94-2.
3. Plants of the new Anthurium have smaller spathes than plants of the selection 91-94-2.
4. Plants of the new Anthurium have salmon pink-colored spathes whereas plants of the selection 91-94-2 have red-colored spathes.

Plants of the new Anthurium can be compared to its sibling, the Anthurium cultivar Atwelve, disclosed in U.S. Plant patent application Ser. No. 09/292,198. However, in side-by-side comparisons conducted in Altha, Fla., plants of the new Anthurium differ from plants of the cultivar Atwelve in the following characteristics:

1. Plants of the new Anthurium are larger and more vigorous than plants of the cultivar Atwelve.
2. Plants of the new Anthurium are more upright with a more open growth habit than plants of the cultivar Atwelve.
3. Plants of the new Anthurium are not as freely branching as plants of the cultivar Atwelve.
4. Plants of the new Anthurium are slightly less freely flowering than plants of the cultivar Atwelve.
5. Leaves of plants of the new Anthurium are larger with more cordate bases than leaves of plants of the cultivar Atwelve.
6. Plants of the new Anthurium have longer petioles than plants of the cultivar Atwelve.
7. Spathes of plants of the new Anthurium are situated closer to the foliage than spathes of plants of the cultivar Atwelve.
8. Spathes of plants of the new Anthurium are larger, more deltoid in shape, have more cordate bases, and have longer more aristate apices than spathes of plants of the cultivar Atwelve.
9. Spathes of plants of the new Anthurium are salmon pink in color whereas spathes of plants of the cultivar Atwelve are red in color.
10. Spathes of plants of the new Anthurium usually have some green coloration in the lobes whereas spathes of plants of the cultivar Atwelve do not have any green coloration.
11. The rear surface of the spathes of plants of the new Anthurium are not as glossy as the rear surface of spathes of plants of the cultivar Atwelve.
12. Spathes of plants of the new Anthurium age more attractively as spathe color darkens with age whereas spathes of plants of the cultivar Atwelve gradually fade in color with age.
13. Spadix rachis of plants of the new Anthurium is yellow-cream in color whereas spadix rachis of plants of the cultivar Atwelve is green in color.

Plants of the new Anthurium can also be compared to its sibling, the Anthurium cultivar Aeighteen, disclosed in U.S. Plant patent application Ser. No. 09/405,606. However, in side-by-side comparisons conducted in Altha, Fla., plants of the new Anthurium differ from plants of the cultivar Aeighteen in the following characteristics:

1. Plants of the new Anthurium are slightly less upright than plants of the cultivar Aeighteen.
2. Plants of the new Anthurium are slightly less freely branching than plants of the cultivar Aeighteen.
3. Leaves of plants of the new Anthurium are broader, more ovate (less lanceolate) with a lower length to width ratio than leaves of plants of the cultivar Aeighteen.
4. Leaves of plants of the new Anthurium lave cordate-shaped bases whereas leaves of plants of the cultivar Aeighteen have obtuse to truncate-shaped bases.
5. Plants of the new Anthurium have longer and thicker petioles than plants of the cultivar Aeighteen.
6. Spathes of plants of the new Anthurium are held more horizontal and less upright than spathes of plants of the cultivar Aeighteen.
7. Spathes of plants of the new Anthurium are larger, more deltoid in shape, and have more aristate apices than spathes of plants of the cultivar Aeighteen.
8. Spathes of plants of the new Anthurium are salmon pink in color whereas spathes of plants of the cultivar Aeighteen are lavender in color.
9. Spathes of plants of the new Anthurium usually have some green coloration in the lobes whereas spathes of plants of the cultivar Aeighteen do not have any green coloration.
10. Spathes of plants of the new Anthurium maintain coloration longer, especially under conditions of high temperature and/or high light than spathes of plants of the cultivar Aeighteen.
11. Spathes of plants of the new Anthurium age more attractively as spathe color darkens with age whereas spathes of plants of the cultivar Aeighteen gradually fade in color with age.
12. Just after spathes have unfurled, spadices of plants of the new Anthurium are bright yellow in color whereas spadices of plants of the cultivar Aeighteen are light lavender in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Anthurium.

The photograph at the top of the first sheet comprises a top perspective view of a typical plant of 'Atwenty' in a 10-cm container about 10.5 months after planting a single tissue culture-produced microcutting.

The photograph at the bottom of the first sheet comprises a close-up view of a typical young inflorescence.

The photograph at the top of the second sheet comprises a close-up view of the upper surface of a typical leaf.

The photograph at the bottom of the second sheet comprises a close-up view of the lower surface of a typical leaf.

DETAILED BOTANICAL DESCRIPTION

The following observations and measurements were recorded on plants grown in Altha, Fla. in polycarbonate-covered greenhouses and under conditions which closely approximate those used in commercial horticultural practice. During the production of these plants, day temperatures ranged from 23 to 28° C., night temperatures ranged from 20 to 23° C., and light level ranged from 800 to 1,500 foot-candles. Plants used for this description were grown as single plants in 10-cm containers and were about 10.5 months from planting a tissue culture-produced microcutting. Fully developed plant structures and organs were used for the following observations and measurements unless otherwise indicated.

In the following description, color references are made to The Royal Horticultural Society Colour Chart except where general terms of ordinary dictionary significance are used. Numerical measurements represent averages from typical plants of 'Atwenty'.

Botanical classification: Anthurium hybrid cultivar Atwenty.

Parentage:

*Female parent.*—Anthurium hybrid cultivar A2, disclosed in U.S. Plant Pat. No. 10,210.

*Male parent.*—Proprietary Anthurium seedling selection identified as code number 91-94-2, not patented.

Propagation:

*Type.*—By tissue culture.

*Time to initiate roots.*—Summer: About 21 days with 25 to 30° C. soil temperatures. Winter: About 18 to 20 weeks with 22 to 27° C. soil temperatures. Winter: About 28 days with 22 to 27° C. soil temperaturesl

*Time to produce a rooted liner.*—Summer: About 16 to 18 weeks with 25 to 30'20 C. soil temperatures.

*Rooting characteristics.*—Primary roots very thick, fleshy, cream to dark pink-colored with yellowish root cap. Lateral roots abundant, thick, cream to dark pink-colored.

Plant description:

*Growth habit.*—Dwarf, open, upright; inverted triangle; not freely branching. Appropriate for 7.5 to 15-cm containers.

*Plant height, soil level to top of leaf canopy.*—About 24.3 cm.

*Plant height, soil level to top of inflorescences.*—About 24.2 cm.

*Plant diameter* (*area of spread*).—About 37.5 cm.

*Plant vigor.*—Very vigorous.

*Crop time.*—About nine months are required to produce a finished plant in a 10-cm container from a single tissue culture-produced microcutting.

*Leaf description.*—Shape, young plants: Ovate; base, obtuse to truncate with cordate tendencies increasing with plant age. Shape, mature plants: Ovate, slightly asymmetrical; apex, acuminate, long; base, cordate. Venation: Prominent near base, less conspicuous near apex. Margin: Entire. Length, mature leaves: About 17.1 cm. Width, mature leaves: About 10.5 cm. Length to width ratio, mature leaves: About 1.6 to 1. Aspect: Midrib slightly oblique with apices slightly pointing upward to almost horizontal. Surface almost flat with lobes curving upwards. Texture/surface: Thick, leathery, glabrous; young leaves, very glossy, older leaves, slightly glossy. Color: Young leaves, just after unfurling, upper surface: More brown and often darker than 147A. Young leaves, just after unfurling, lower surface: Darker than 148A. Mature leaves, upper surface: 147A or slightly darker. Mature leaves, lower surface: Between 147B and 146A. Mature leaves, venation, upper surface: Most of midrib and proximal portions of primary veins, 146B; remaining veins similar to or slightly lighter than surrounding tissue. Slight brownish anthocyanin coloration sometimes present near petiole junction. Mature leaves, venation, lower surface: Proximal more than half of midrib varies between 144A, 144B, 146B and 146C.

*Petiole.*—Length, primary shoot: About 15.2 cm. Diameter, primary shoot, just below geniculum: About 3.5 mm. Geniculum length: About 1.4 cm. Geniculum diameter: About 4.6 mm. Petiole wings length, primary shoot: About 2.1 cm. Petiole wings width, primary shoot: About 5.5 mm. Color: Young leaves, just after unfurling: Front, between 200D, 165A and a color darker than 199A often with various amounts of 148A. Rear, 146B with various amounts of 199A especially distally or at mid-section. Mature leaves, winged area: 146A with some 147B. Mature leaves, above winged area: Front, 146A, 146B and 148A just below geniculum; slight brownish anthocyanin coloration often present in distal portion of petiole. Rear, 146B; distally, lighter and more yellow, between 146C and 144A just below geniculum. Geniculum: Front, 146A; rear, 144A.

Inflorescence description:

*Arrangement.*—Spathes with spadices held just above the leaves on straight, strong and thick peduncles. Flowering structures arise from leaf axils. About 3.5 inflorescences per plant.

*Time of flowering, time to flower.*—Flowering year-round. Flowering commences about 8 months after planting of a tissue culture-produced microcutting.

*Inflorescence longevity.*—Spathes of plants of the new Anthurium are long-lasting. During the fall, spathes maintain typical salmon pink color for about 2 to 2.5 months. With subsequent development, spathe color gradually darkens, but retains ornamental value for several months beyond maturity. After about 4.5 months, inflorescences are still attractive with spathes reddish brown in color with green undertones, dark green lobes, and portions of veins, red in colorp; spadix, dark green.

*Frangrance.*—Strong, pleasant.

*Spathe.*—Shape: Deltoid; apex, aristate; base, cordate. Margin: Entire. Texture: Thick, leathery, glabrous, slightly puckered, glossy. Aspect: Almost flat; midrib horizontal to slightly oblique, about 65° from vertical. Length: About 8.3 cm. Width: About 7.6 cm. Length to width ratio: About 1.1 to 1. Color: Before unfurling: most similar to 34D; base flushed with green. Portions of primary veins at the base, 144A; apex, 144B. Just after unfurling, front surface: Similar to or lighter than 42D, but darker than 35C; lobes flushed with green. Portions of primary veins in the lobes, 144A to 144B; apex, 144B to 144C. Mature, front surface: Varies between 35C, 35D, 37A, 37B, 39B, 39C and combinations thereof; lobes often flushed with green. Portions of primary veins in the lobes, 144A to 144B. Apex, 144B to 144C. Mature, rear surface: Varies between 35C, 35D, 37B, 37C, 39C and combinations thereof; lobes flushed with green. Midrib and veins, especially in proximal part, 144A to 144B; apex, 144B. More glossy than front surface.

*Spadix.*—Length: About 5 cm. Diameter: About 8.2 mm. Shape: Columnar, slightly tapering in distal zone, sometimes slightly curved. Cross-section: Approximately round; rachis, cream in color. Aspect: About 65 to 80° to spathe; sometimes slightly bent towards spathe. Color: Just after spathe unfurling: Proximal zone, varies between 4B and 5C; distal zone, darker and more green, merging with 154A at apex. Mature: Proximal zone, with pistils, varies between 158B and 159C; merging with 4A and 5B at distal zone, without pistils; merging with 154A to 154B at apex.

*Flowers.*—Quantity: About 7 or 8 per linear cm at mid-section. Pistil, mature, appearance: About 2 mm in length; protrudes less than 0.5 mm beyond perianth; cross-section rectangular, about 1.2 by 1 mm; apex, flat. Stamen, mature, appearance: Do not protrude beyond perianth; flat, firmly pressed against pistils; about 1.2 by 0.7 mm in size. Pollen: Not observed to date. Seed development: Not observed to date.

*Peduncle.*—Length: About 14.5 cm. Diameter: About 4.2 mm. Stipe length: About 2.3 mm. Color: Young: Just below spathe, 146A; proximally lighter; near base, 144A. Mature: Front, just below spathe, 144A; proximally darker; near base, 146A with some 147B. Rear, below spathe, 146B; proximally darker; near base, 146A.

Disease/insect resistance: Plants of the new Anthurium grown in commercial greenhouses have not shown any unusual susceptibility to pathogens or insects common to Anthurium.

It is claimed:

1. A new and distinct cultivar of Anthurium plant named 'Atwenty', as illustrated and described.

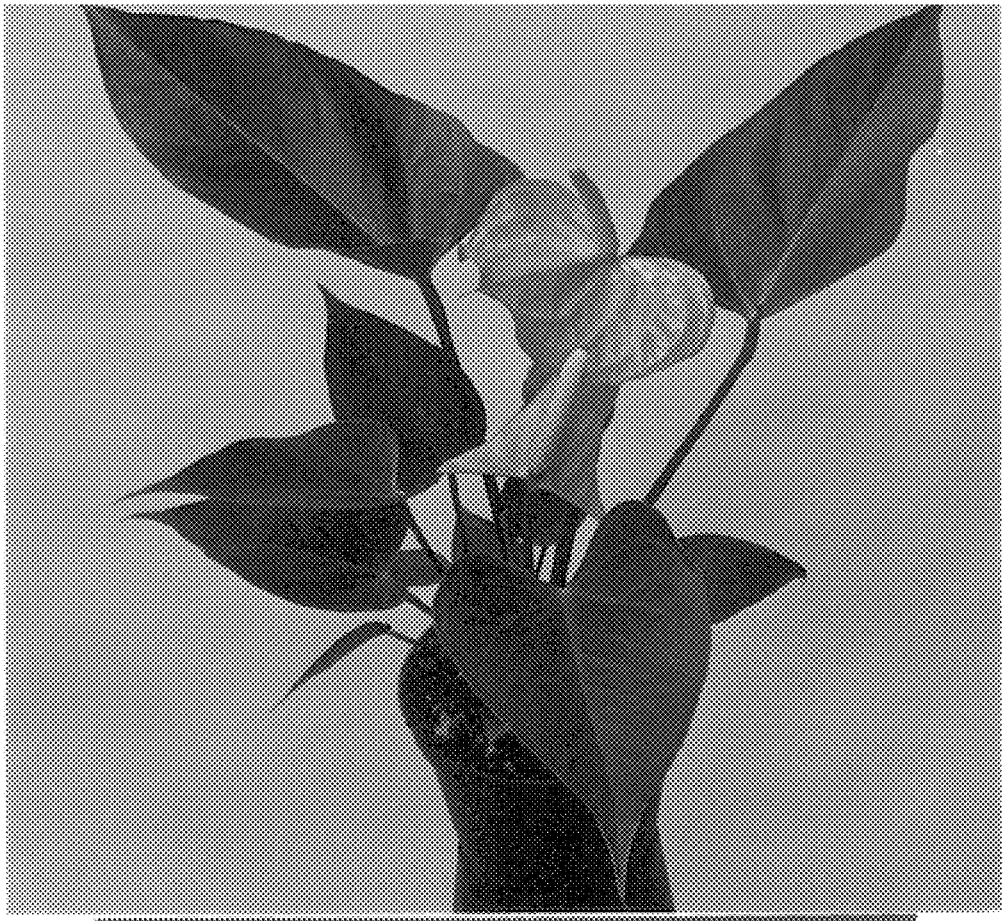
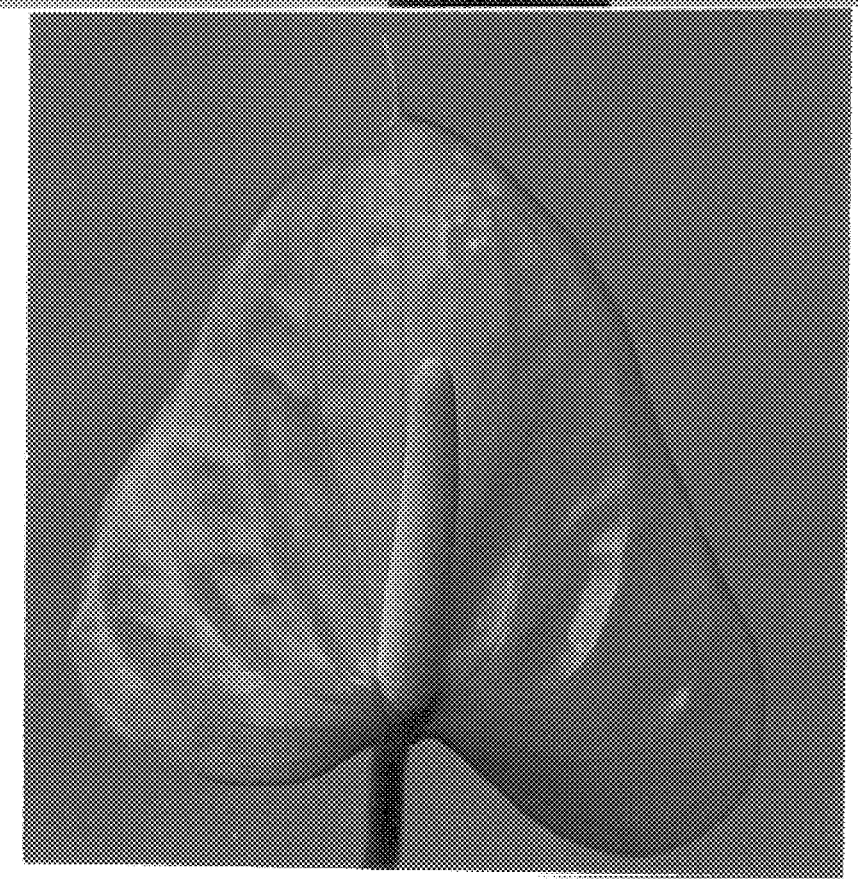

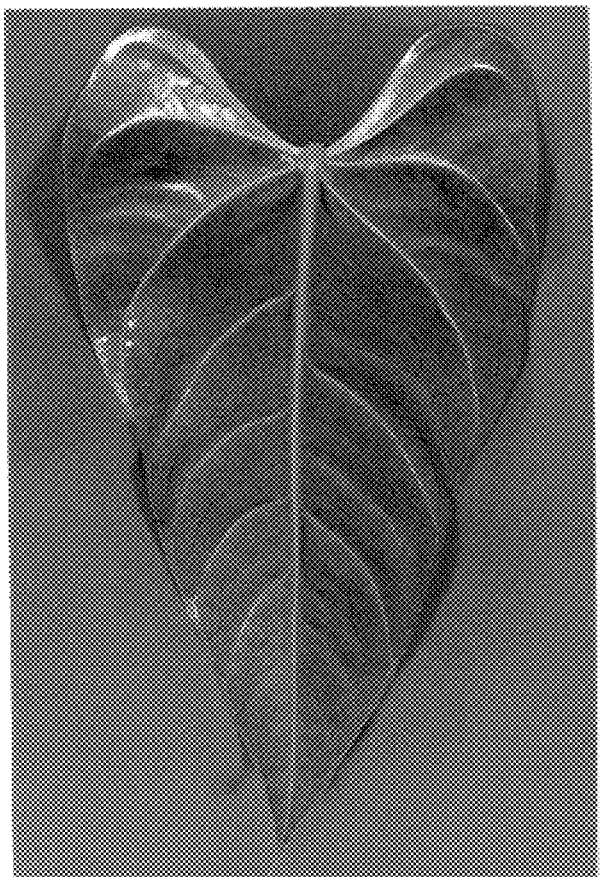
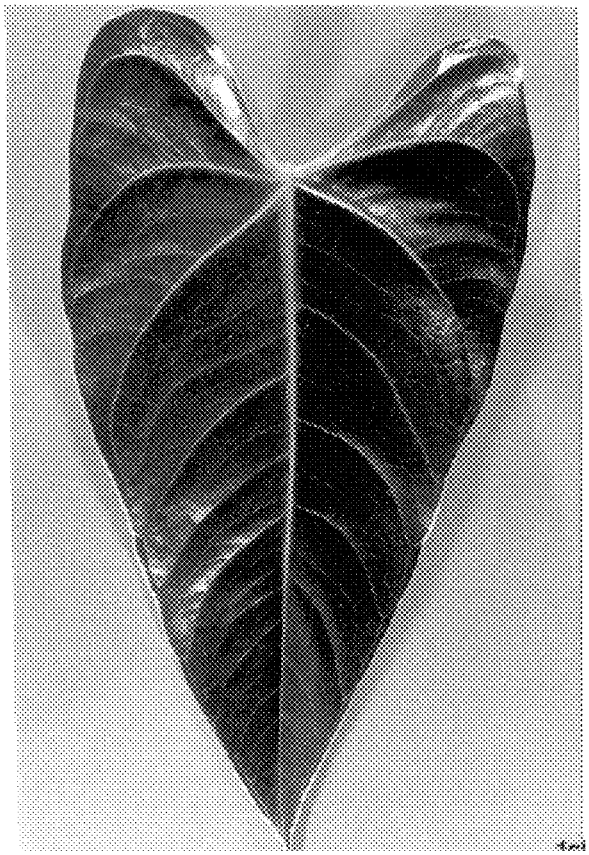

* * * * *